United States Patent
Hontz et al.

(10) Patent No.: US 7,577,580 B2
(45) Date of Patent: Aug. 18, 2009

(54) SYSTEM AND METHOD FOR PROVIDING PHARMACEUTICAL DATA IN A SECURE AND AFFORDABLE MANNER

(75) Inventors: Karrie Hontz, Collegevile, PA (US); Stephen Mann, Columbia, SC (US); Valerie Dilworth, Harleyville, PA (US)

(73) Assignee: IMS Software Services Ltd., Plymouth Meeting, PA (US)

( * ) Notice: Subject to any disclaimer, the term of this patent is extended or adjusted under 35 U.S.C. 154(b) by 182 days.

(21) Appl. No.: 10/524,925

(22) PCT Filed: Aug. 19, 2003

(86) PCT No.: PCT/US03/25969

§ 371 (c)(1),
(2), (4) Date: Nov. 23, 2005

(87) PCT Pub. No.: WO2004/017203

PCT Pub. Date: Feb. 26, 2004

(65) Prior Publication Data

US 2006/0106639 A1    May 18, 2006

Related U.S. Application Data (60) Provisional application No. 60/404,451, filed on Aug. 19, 2002.

(51) Int. Cl.
*G06F 17/30* (2006.01)
*G07G 1/00* (2006.01)

(52) U.S. Cl. ........................................ 705/10
(58) Field of Classification Search .................... 705/10
See application file for complete search history.

(56) References Cited

U.S. PATENT DOCUMENTS

| 4,823,265 A | 4/1989 | Nelson |
| 5,160,726 A | 11/1992 | Josephson et al. |
| 5,526,257 A * | 6/1996 | Lerner ......................... 705/10 |
| 5,630,127 A | 5/1997 | Moore et al. |
| 5,704,044 A | 12/1997 | Tartar et al. |
| 5,737,396 A | 4/1998 | Garcia |
| 6,078,893 A | 6/2000 | Ouimet et al. |
| 6,243,615 B1 | 6/2001 | Neway et al. |
| 6,249,774 B1 | 6/2001 | Roden et al. |
| 6,457,007 B1 | 9/2002 | Kikuchi et al. |

(Continued)

FOREIGN PATENT DOCUMENTS

WO      WO/03/085488       * 10/2003

*Primary Examiner*—Christian LaForgia
(74) *Attorney, Agent, or Firm*—Baker Botts LLP (57) ABSTRACT

A system and method for evaluating the performance of a first at least one of a plurality of outlets is provided. The system includes a computer system configured to execute a data access application, wherein the data access application includes a plurality of user accounts, wherein each of the plurality of user accounts includes a user group, and wherein a second at least one of the plurality of outlets is associated with the user group. The system also including a data storage device configured to store market measures from a portion of the plurality of outlets and industry-standard market measures, wherein the data access application allows a user to access the industry-standard market measures and data associated with the outlets associated with the user group of user's user account.

17 Claims, 9 Drawing Sheets

U.S. PATENT DOCUMENTS

| | | |
|---|---|---|
| 6,609,106 B1 | 8/2003 | Robertson |
| 6,615,182 B1 | 9/2003 | Powers et al. |
| 7,165,077 B2 * | 1/2007 | Kalies .................... 707/104.1 |
| 2002/0107719 A1 * | 8/2002 | Tsang et al. ................. 705/10 |
| 2002/0184072 A1 * | 12/2002 | Linde et al. .................. 705/10 |
| 2003/0050825 A1 * | 3/2003 | Gallivan et al. .............. 705/10 |
| 2004/0088190 A1 * | 5/2004 | Timmons et al. ............... 705/2 |
| 2004/0148196 A1 * | 7/2004 | Kalies ........................... 705/2 |
| 2005/0071193 A1 * | 3/2005 | Kalies ........................... 705/2 |
| 2006/0053032 A1 * | 3/2006 | Weiler et al. ................... 705/2 |
| 2006/0074695 A1 * | 4/2006 | Houston et al. ................ 705/1 |

* cited by examiner

SYSTEM AND METHOD FOR PROVIDING PHARMACEUTICAL DATA IN A SECURE AND AFFORDABLE MANNER

RELATED APPLICATION

This application is a national phase of International Patent Application No. PCT/US03/025969, filed Aug. 19, 2003, published on Feb. 26, 2004 as International Patent Publication No. WO 04/017203, which claims priority from U.S. Provisional Patent Application Ser. No. 60/404,451 filed Aug. 19, 2002, entitled "RxInsight Security Procedures," each of which are incorporated by reference in their entireties herein, and from which priority is claimed.

BACKGROUND OF THE INVENTION

1. Technical Field

The present invention relates to security techniques for customer accessible databases.

2. Background Art

Pharmacies and wholesale pharmaceutical outlets have engaged various tools to evaluate their market share and monitor other key performance indicators in their national or local operating areas. One approach is to access company data, e.g., dispensed prescriptions, cash pricing, managed care contract rates, and generic dispensing ratios, and to compare that to industry standard market measures. For example, a pharmacy chain might determine their own company's prescription dispensing growth is 3% in the Philadelphia market, while the overall prescription volume is growing at 8%, and therefore determine that the chain is losing market share.

In general, such pharmaceutical outlets treat their own market performance information to be a highly protected trade secret. Accordingly, there exists a need for a technique which provides a secure environment to provide information services to these chains, in a cost-effective manner, while protecting the confidentiality of these data, and reducing opportunity for error or corruption in the data.

SUMMARY OF THE INVENTION

An object of the present invention is to provide a technique for permitting pharmaceutical outlets to evaluate their market share in a secure environment.

Another object of the present invention is to provide information services to pharmaceutical outlets in a cost-effective, confidential accurate manner.

In order to meet these and other objects of the present invention which will become apparent with reference to further disclosure set forth below, the present invention provides a database security access methodology, combined with a software application and sophisticated reference files and/or database files which enable pharmacy outlets to access confidential pharmaceutical information related to their respective companies, from one single database which houses all chains' data.

The technique is cost-effective since the cost of populating, updating, and maintaining this information, housed on a central platform, can be spread across all pharmacy chains subscribing to the database. The chains do not have to incur the costs of purchasing a hardware platform and managing it themselves. There is no time delay from when the current month's information is available, and the chains' receipt of the data, and they can log on and access it immediately upon completion of the data load at the data warehouse. There is no delay in transmitting or shipping the data to a chain's data center and then waiting for the data load to occur there. Additionally, the data warehouse does not have to generate multiple large data marts for each chain that desires access to these data, thus resulting in additional cost savings, minimizing risk of data corruption in reproduction, and facilitating maintenance and updates to the data by only having one data warehouse to update versus many.

A system and method for evaluating the performance of a first at least one of a plurality of outlets is provided. The system includes a computer system configured to execute a data access application, wherein the data access application includes a plurality of user accounts, wherein each of the plurality of user accounts includes a user group, and wherein a second at least one of the plurality of outlets is associated with the user group. The system also including a data storage device configured to store market measures from a portion of the plurality of outlets and industry-standard market measures, wherein the data access application allows a user to access the industry-standard market measures and data associated with the outlets associated with the user group of user's user account.

In another advantageous embodiment of the present invention, a system and method for evaluating the performance of a first at least one of a plurality of outlets is provided. The system includes a computer system configured to execute a data access application, wherein the data access application includes a plurality of user accounts, wherein each of the plurality of user accounts includes a user group, and wherein a second at least one of the plurality of outlets is associated with the user group. The system also including a data storage device configured to store market measures from a portion of the plurality of outlets and industry-standard market measures, wherein the data access application allows a user to access the industry-standard market measures and data associated with the outlets associated with the user group of user's user account.

The accompanying drawings, which are incorporated and constitute part of this disclosure, illustrate preferred embodiments of the invention and serve to explain the principles of the invention.

Throughout the drawings, the same reference numerals and characters, unless otherwise stated, are used to denote like features, elements, components, or portions of the illustrated embodiments. Moreover, while the present invention will now be described in detail with reference to the FIGS., it is done so in connection with the illustrative embodiments.

DETAILED DESCRIPTION OF THE PREFERRED EMBODIMENTS

Figure 1:
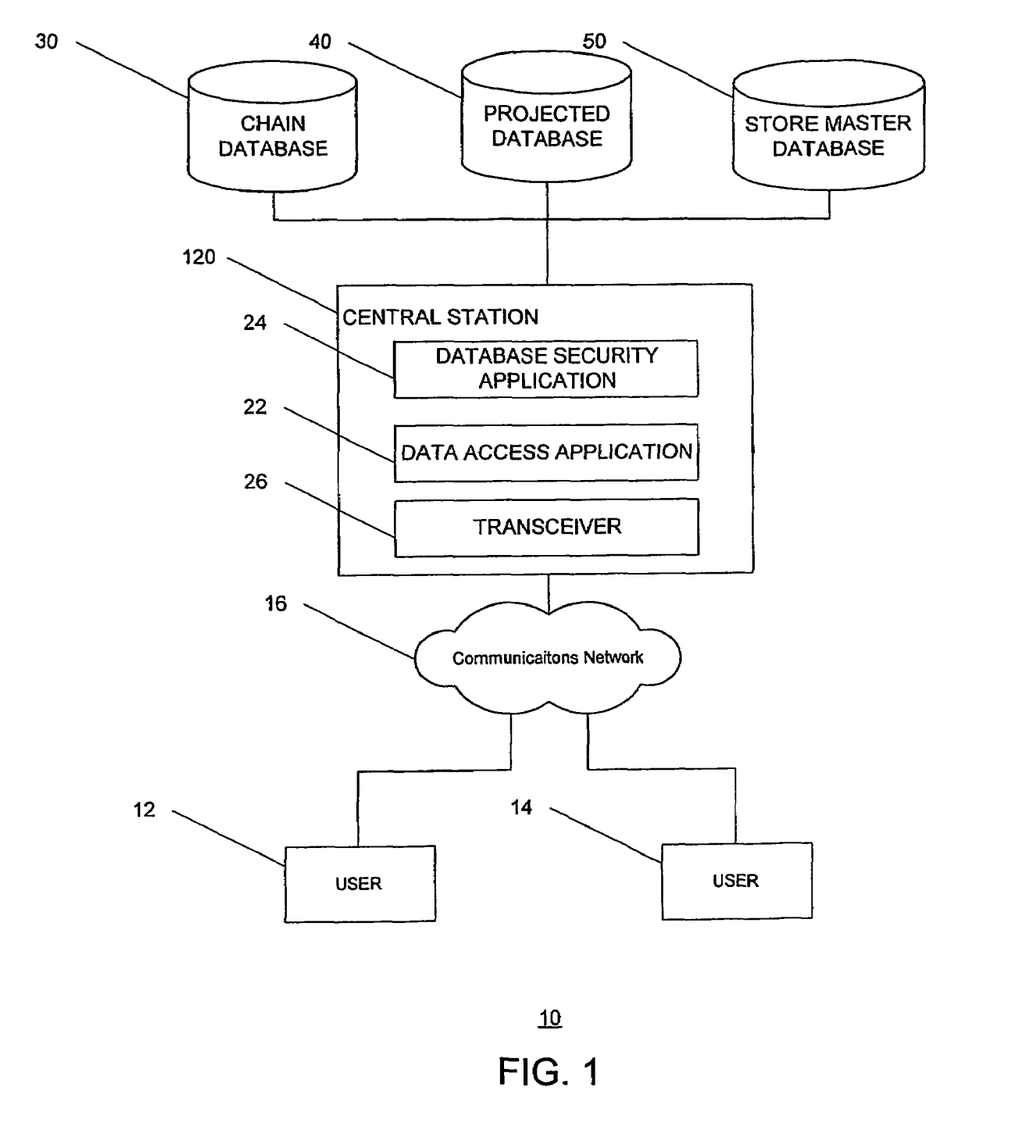
FIG. 1 is a functional diagram of an exemplary method in accordance with the present invention.

FIG. 1 illustrates an exemplary embodiment of a system and method for permitting retail outlets or a chain of retail outlets to evaluate their performance in a particular market in a secure environment. Generally, the exemplary system and method deliver proprietary sales data and market sales data to a user, thus allowing the user to appreciate the performance of the user's retail outlet or chain of retail outlets. Specifically, the exemplary methods and systems deliver proprietary pharmaceutical chain data and pharmaceutical market data to a user, thus allowing the user to appreciate the performance of the user's pharmaceutical retail outlet or chain of pharmaceutical retail outlets.

FIG. 1 illustrates a block diagram of a pharmaceutical data analysis system 10. The data analysis system 10 includes a communications network 16, the central server 120, a chain database 30, a projected database 40 and a store master database 50. The pharmaceutical data analysis system 10 allows a user 12, 14 to upload market measures for a current month and receive information pertaining to pharmaceutical retail outlet, a chain of pharmaceutical retail outlets, and/or a portion of the chain of pharmaceutical retail outlets.

In a preferred embodiment, the communications network 16 is the Internet. In another preferred embodiment, the communications network 16 is a private network.

The user 12 utilizes the central station 120 by using his or her user account and logging into a data access application 22 through the communications network 16. The central station 120 is a server, which includes a transceiver 26. Data may be transmitted or received by the central station 120 through the transceiver 26. The data access application 22 and a database security application 24 run on the central station 120. The user may use the data access application 22 and indirectly the database security application 24 to upload market measures for a current month, receive information, generate reports, and the like.

In a preferred embodiment, multiple transceivers may be utilized. In another preferred embodiment, the transceiver 26 is a network interface card.

The users 12, 14 upload market measures for a particular month on a monthly basis. The data access application 22 and the database security application 24 receive the market measures from the users 12, 14 and populate the chain database 30, the projected database 40 and the store master database 50 with market measures for a current month. Each of the chain database 30, the projected database 40 and the store master database 50 are Oracle-based relational databases. The chain database 30 houses market measures including all pertinent transactions submitted to the system 10 from a particular retail establishment's retail transaction systems, and are stored in a manner which enables each retail establishment's data to be identifiable and retrievable. For example, information identifying the particular pharmacy may be included. The retail establishment can be a single establishment or a chain of establishments.

The projected database 40 houses aggregated, projected, industry-standard market measures. The technique for storing and generating the aggregated, projected, industry-standard market measures is described hereinbelow with reference to FIGS. 2-9. The projected database 40 provides the benchmark market data for retail establishments, chains of retail establishments or portions of chains of retail establishments to compare their performance to that which is occurring in an overall relevant marketplace.

The store master database 50 is also updated on a monthly basis. The store master database 50 is a proprietary reference database, also stored in an Oracle-based relational data table, which contains the relationships between each retail store in a geographic area, its local operating company name called the Organization Name, and its Parent company. Preferably, the geographic area is a country, for example: the United States. The store master database 50 contains information describing the many diverse relationships that exist as large corporate entities continue to acquire local retail chains and independent stores offering the product or products being tracked, while maintaining the local operating business name. An example of data stored in the store master database 50 follows as Table I:

TABLE I

| Store Name/Address | Organization Name | Parent Name |
| --- | --- | --- |
| ABC DRUGS | Cutter Supply, Inc. | Diamond Valu Worldwide |
| Jewel's Crystal Mart | Colorful Savings Co. | Diamond Valu Worldwide |
| Lucky's Save-a-Lot | Carrot-Top Enterprises | Diamond Valu Worldwide |
| Outlet A | Discount Supplies | Corporation A |
| Outlet B | Discount Supplies | Corporation A |
| Sunny's Selections | Clarity Surplus | Diamond Valu Worldwide |

In order to provide secure access to the databases 30, 40, 50, they are accessed by users 12, 14 at the retail chain headquarters via a commercially available web-based decision support tool: the data access application 22. Since it is critical that each user 12, 14 have access to only a portion of the data contained in the database 30 and complete access to the data contained in the projected database 40, several layers of security are required.

In a preferred embodiment, the data access application 22 is provided by Business Objects.

Each user 12, 14 has an account including a username and password. Each account is also associated with at least one parent name, for example a user account may be associated with the parent name "Diamond Valu Worldwide." Upon establishing the new user account, the user is given access to all data corresponding to a particular parent entity by default. If a user's account is associated with Diamond Valu Worldwide, the user may access data associated with each of the stores that are also associated with Diamond Valu Worldwide, i.e., ABC Drugs, Jewel's Crystal Mart, Lucky's Save-A-Lot, and Sunny's Selections. The user would not be able to access data corresponding to Outlet A and Outlet B, because that data is associated with the parent "Corporation A." The user's access may be restricted to a portion of the data corresponding to the parent entity. A user account may be given access to data corresponding to all stores associated with a parent entity, all stores associated with a particular organization of a parent entity, a particular store or another group of stores. Using the example above, Diamond Valu Worldwide may create a new user account for Jewel's Crystal Mart's manager to see only data pertaining to Jewel's Crystal Mart.

In order to realize these differing levels of security, the database security application 24 utilizes Oracle security procedures. A "user group" is developed, associating specific rows in the database to a given parent name, organization name or other subset of retail establishments. A user account associated with a particular user group is only able to access the rows associated with the user group. If the store master database 50 included the data as described by Table I, a Diamond user group could be developed based upon the parent name "Diamond Valu Worldwide." A user account associated with the Diamond user group would be able to access the rows associated with ABC Drugs, Jewel's Crystal Mart, Lucky's Save-a-lot and Sunny's Selections, but not the rows associated with Outlet A and Outlet B. It should be noted that all user groups are provided access to the entire projected database 40.

In a preferred embodiment, a user group may be associated with more than one parent name.

A level of security is realized using the data access application 22. Using security procedures of the data access application 22, a new user account may be established which enables access to the data access application 22 interface. The new user account is associated with a user group, which is developed as described above. In the example above, a new user account for "John Smith" could be associated with the "Diamond" user group.

A further level of security is established at the data element level. Each parent entity or organization, may submit a chain attribute data file. The chain attribute data file is merged into the chain database 30 and/or the projected database 40. This file contains chain-specific attributes, from which customized reports and analytic measures may be created. For example, a parent entity or organization could send data to the store master database 50, which would group stores into districts or regions, in order to generate relevant reports for their district or regional managers. The chain-specific attributes are also linked into the database via the parent name and the user group security noted above. These data are not visible to any user outside of the retail chain's user group.

Figure 2:
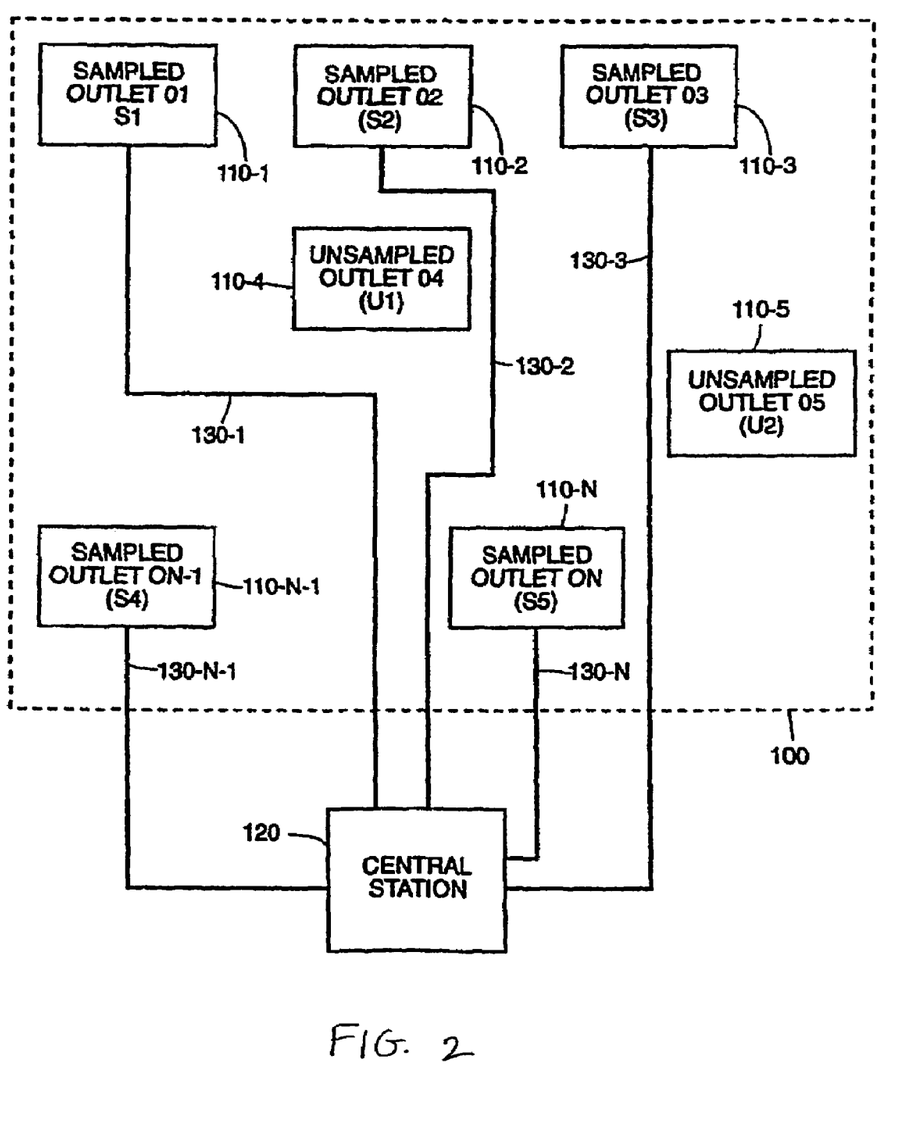
FIG. 2 is a block diagram showing an arrangement of sales outlets and a processing station illustrative of an embodiment of the invention.

FIG. 2 depicts an arrangement illustrating a first embodiment of the invention in which product sales at unsampled sales outlets are estimated. In FIG. 2, there are shown an area 100, sampled sales outlets 110-1, 110-2, 110-3, 110-N-1 and 110-N and unsampled sales outlets 1104 and 110-5 in the area 100 and a central station 120. Each of sampled outlets 110-1, 110-2, 110-3, 110-N-1 and 110-N may preferably be coupled via a line of lines 130-1 through 130-N to the central station 120.

In FIG. 2, the outlets may be pharmacies or other type of retail stores or distribution establishments all of which distribute a particular product. The outlets are at various locations in the area 100. While there are 7 outlets shown in FIG. 2 for purposes of illustration, it is to be understood that there are generally hundreds or thousands of outlets which are not restricted to a given area. The location of each outlet is generally known in terms of latitude and longitude from available census data or in terms of zip code centroids from Post Office data. Accordingly, the distances between pharmacies can be determined. Product sales data generated at each outlet $S_n$ (e.g., 110-1) is preferably transferred to the central station 120 via a line (e.g., 130-1). Unsampled outlets $U_n$ (e.g., 110-4 or 110-5) in the area 100 are not coupled to the central station or, if coupled, do not supply valid sales data so that only an estimate of the sales volume of the particular product can be made.

A single area 100 is shown in FIG. 2 for purposes of illustration only. According to the invention, the estimation of sales activity at an unsampled outlet U is formed on the basis of the sales activity at the sampled outlets S in a neighborhood of the unsampled outlet U. The neighborhood of an unsampled outlet U may be defined as the N closest sampled outlets S which is different for each unsampled outlet and not as a predefined geographic area. In an urban area, the neighborhood of closest sampled outlets may all be located within a short distance of the unsampled outlet. In a rural area, the neighborhood of N closest sampled outlets nay spread over distances. Consequently, each unsampled outlet has its own neighborhood area which varies according to the distances to the nearest N sampled outlets. Advantageously, the correlation of sales activity data is not restricted to a predetermined geographic area as in the prior art.

Figure 3:
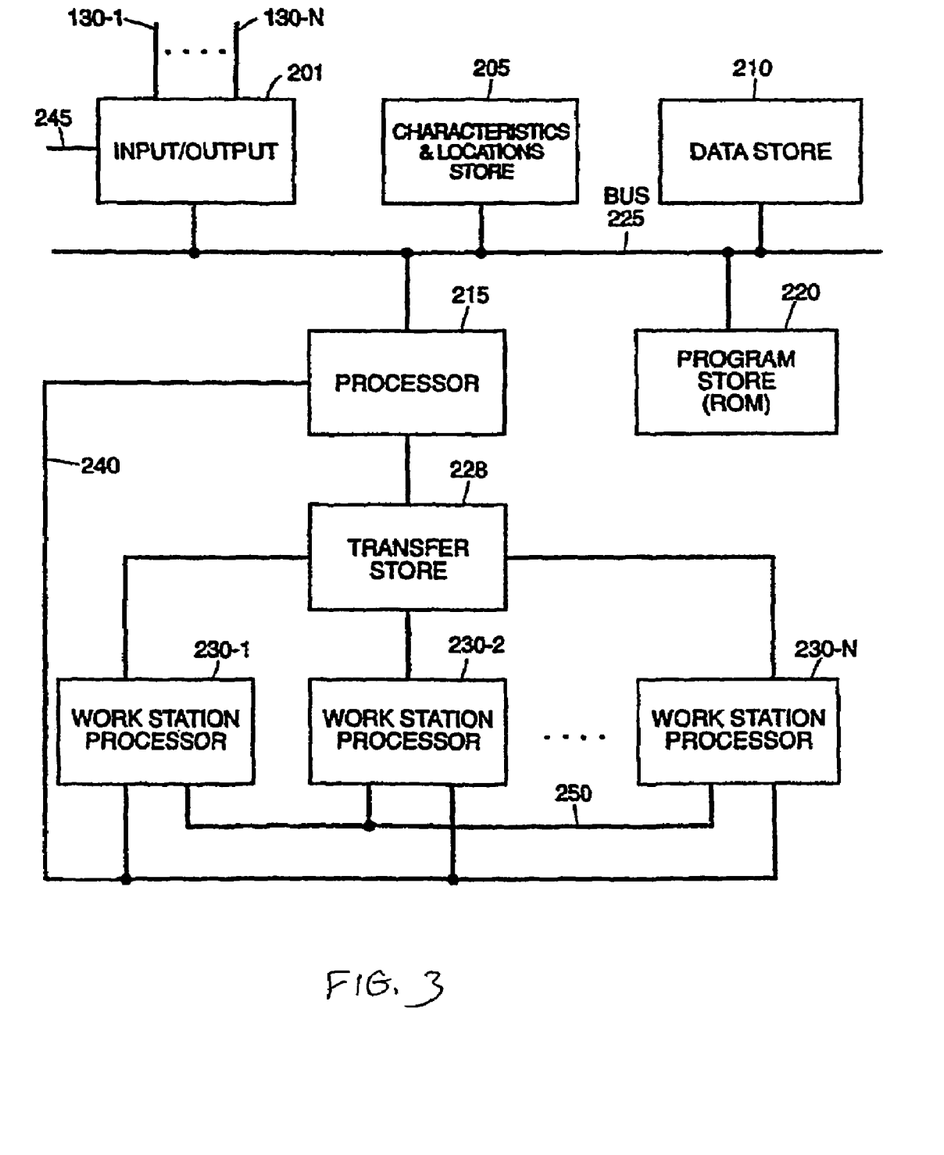
FIG. 3 is a block diagram of a processing system that may be used as the central station of FIG. 2.

FIG. 3 depicts a block diagram of the central station 120 of FIG. 2 which includes an input/output unit 201, a characteristics and location store 205, a sales data store 210, a processor 215, a program store 220, a bus 225, a transfer store 228 and work station processors 230-1 through 230-N. Input/output 201 is coupled to bus 225 and is also coupled to the sampled outlet lines 130-1 to 130-N and to output line 245. The characteristics and location store 205, the prescription data store 210 and the program store 225 are coupled to the bus 225. The Processor 215 is coupled to the bus 220, the transfer store 228 and is also coupled to work station processors via a control line 240. The transfer store 228 is coupled to work station processors 230-1 to 230-N and the work station processors are coupled together through a network 250. Characteristics signals stored in store 205 may include signals representing the type of outlet or the total sales of all products at the outlet. This type of data is available from sources such as Drug Distribution Data (DDD®) available from IMS America, Plymouth Meeting, Pa. DDD® is a trademark of IMS America. Program store 220 stores instruction signals that control the operation of the processor 215 and provide parameter signals to determine the operation of work station processors 230-1 through 230-N through the processor 215 and control line 240.

The sales outlet data received by input/output 201 from sales outlets which may exceed $2 \times 10^9$ records each having between 88 and 1000 bytes is transferred to data store 210. In view of the large amount of data to be processed, the processing is divided between the processor 215 and the work station processors 230-1 through 230-N. Information signal arrays produced in the processor 215 are transferred to work station processors 230-1 through 230-N through the transfer store 228. Each information signal array from the processor 215 placed in the transfer store 228 is divided into N portions. A preassigned portion of the information signal array in the transfer store is supplied to each of work station processors 230-1 through 230-N and the processing of the portions in the work stations 230-1 through 230-N is controlled by signals from the processor 215 via the control line 240. After the processing of the information signal array portions in the work station processors, the processed information signal array portions are merged into one processed information signal array which is returned to transfer store 228 from the work station processors. The returned information signal array in the transfer store 228 is then further processed in the processor 215 to produce estimate sales volume results. The operation of the system of FIG. 3 will be further described in connection with the estimation arrangements shown in FIGS. 4-8.

Figure 4:
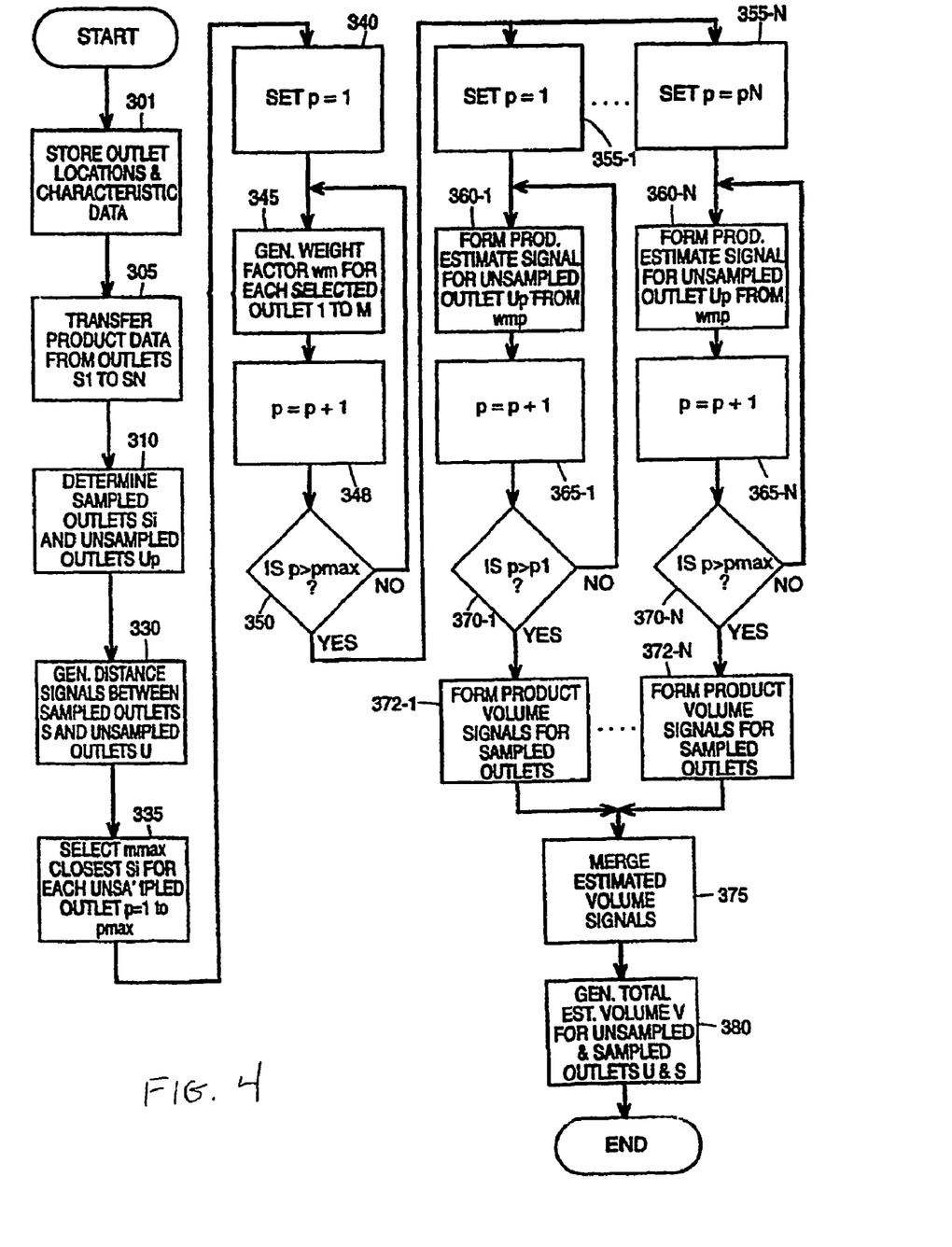
FIG. 4 is a flow chart showing the estimation of prescription sales at an outlet that is illustrative of the invention.

FIG. 4 depicts a flow chart illustrating the operation of the central station 120 of FIG. 2 in estimating the volume of sales of a particular product at an unsampled outlet such as outlet O4 or outlet O5 in FIG. 2. The operations depicted in the flow chart of FIG. 4 are performed by processor 215 and work station processors 230-1 to 230-N of FIG. 3 under control of instruction signals from in the program store 220. In the flow chart of FIG. 4, product data from outlets O1, O2, O3, ON-1 and ON are transferred to the input/output unit 201 preferably via corresponding lines 130-1 through 130-N in step 301. Transferred data is stored in outlet sales data store 210. A data transfer from an outlet may occur for each sales transaction or may include a number of transactions for a prescribed period of time. At preset intervals, the sales data is sent to processor 215 and therein is evaluated in step 310 to determine the sampled outlets Si and the unsampled outlets Up in the processor 215. Unsampled outlets may include outlets transferring data evaluated as invalid.

Figure 5:
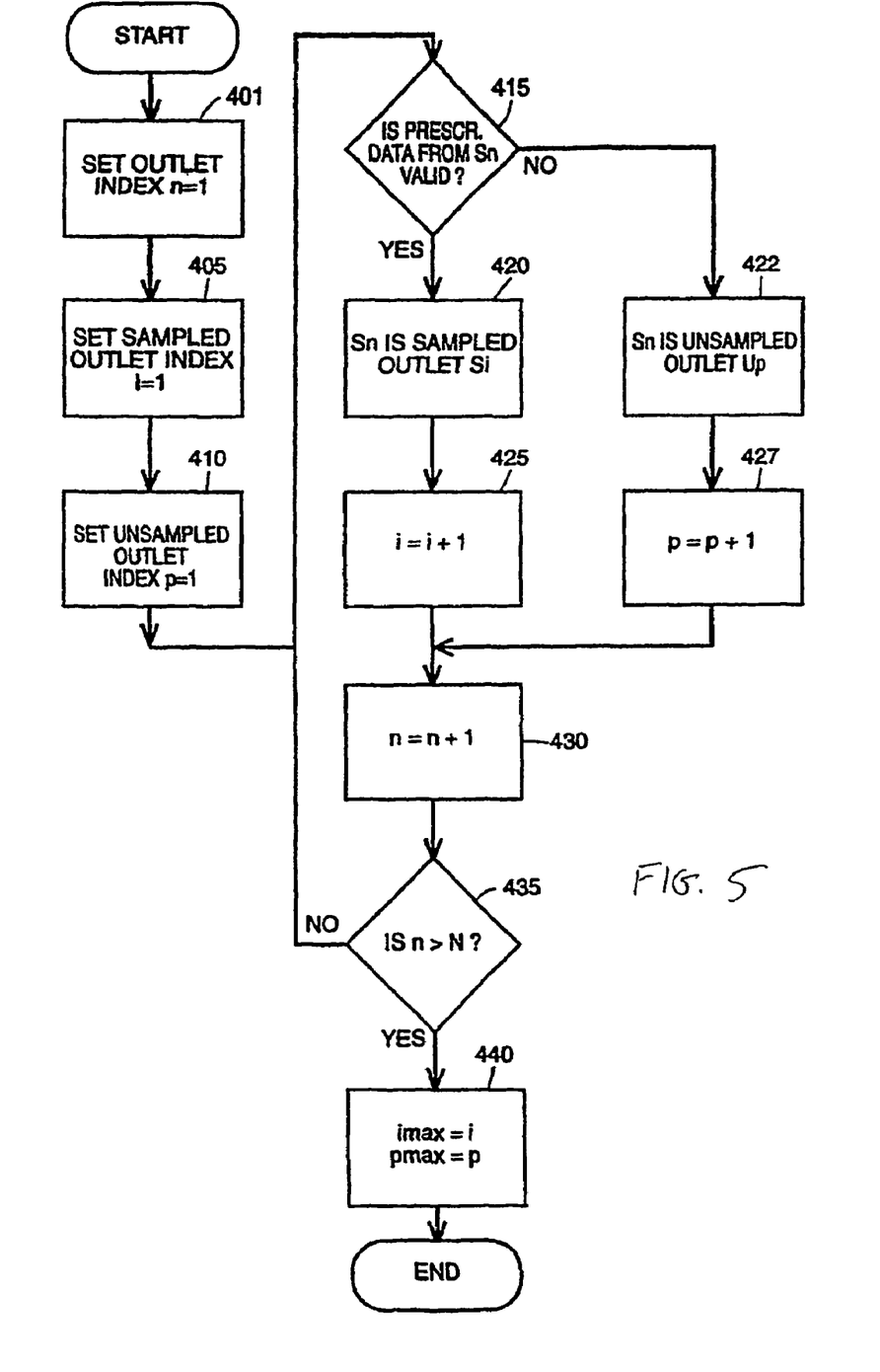
FIG. 5 is a flow chart showing the determination of sampled and unsampled outlets of FIG. 4 in greater detail.

FIG. 5 shows a method of determining sampled and unsampled outlets in greater detail. Referring to FIG. 5, an outlet index n for the outlets O1, O2, . . . , ON is set to 1 in step 401. A sampled outlet index i and an unsampled outlet index p are set to 1 in steps 405 and 410. The sales data for the particular product from each outlet On is checked in decision step 415 to determine if the data is valid (i.e., meets predetermined criteria). If the data is judged to be valid in step 415, the outlet On is classified as a sampled outlet Si in step 420 and the index i is incremented in step 425. When no data is available for the outlet On or the data is not accepted as valid in step 415, the outlet On is classified as an unsampled outlet Up in step 422 and the index p is incremented in step 427. The index n is then incremented in step 430. Until index n is greater than N for the last outlet ON, step 415 is reentered from decision step 435. When all of the outlets O1 through ON have been classified as sampled outlets and unsampled outlets, the last value of index p (pmax) and the last value of index i (imax) representing the number of unsampled outlets and the number of sampled outlets are stored in data store 210 (step 440).

As shown in FIG. 2, there are five sampled outlets 110-1 (O1), 110-2 (O2), 110-3 (O3), 110-N-1 (ON-1) and 110-N (ON) which are designated S1, S2, S3, S4 and S5 from the processing of FIG. 5 and two unsampled outlets 110-4 (O4) and 110-5 (O5) which are designated as U1 and U2 from processing of FIG. 5. Unsampled outlet U1 is located in the central portion of the area 100 and is surrounded by sampled outlets S1 through S5. Unsampled outlet U2 is located at one edge of the area 100, is closest to sampled outlet S5 and most remote from sampled outlet S1. Priorly known techniques based an estimate of the sales volume of a product at an unsampled outlet on the sales volume of the product for the geographic area. Since the sales outlets have different characteristics (e.g., size and location) and have sales related to outlets outside a particular area, estimates based on the overall sales volume in a particular area as in the prior art are biased. In accordance with the invention, an estimate of sales volume of a particular product at a sales outlet is based on the known sales volume of other outlets according to the distances between the sales outlet and the other outlets and the particular characteristics of the outlets independent of any geographic area. By using the outlet characteristics and the distances, an unbiased and more accurate estimate may be determined.

Signals corresponding to the distances between unsampled outlet U1 and sampled outlets S1 through S5 and the distances between outlet U2 and sampled outlets S1 through S5 are then formed in step 330. In step 335, the mmax closest sampled outlets to unsampled outlet p are selected. The selection is performed in the processor 215. mmax may be chosen according to the total number of sampled outlets. The selection of sampled outlets associated with each unsampled outlet is shown in greater detail in FIG. 6.

Figure 6:
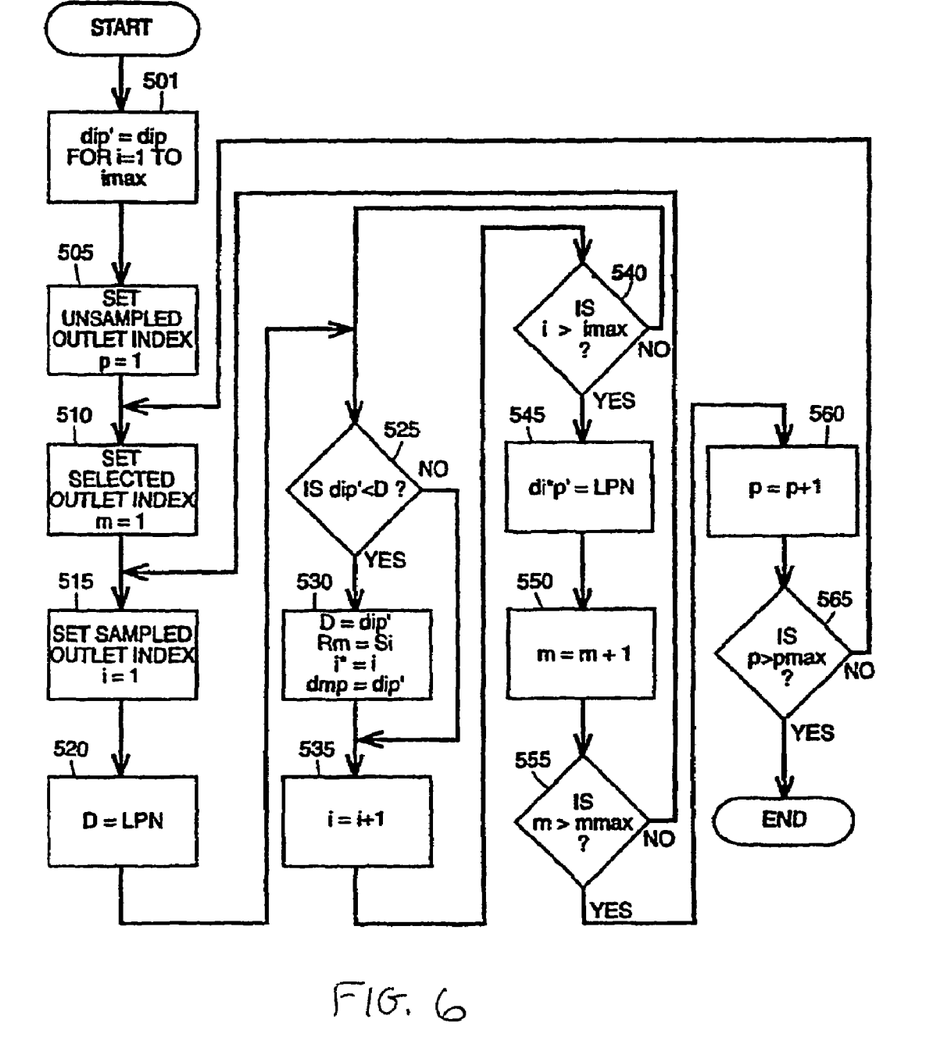
FIG. 6 is a flow chart showing the selection of the group of sampled outlets for each unsampled outlet in greater detail.

With reference to FIG. 6, a set of distance signals dip' for sorting is generated in step 501 corresponding to the distance signals dip generated in step 330. The unsampled outlet index p is set to one in step 505. A selected outlet index m is set to one in step 510 and the sampled outlet index i is set to one in step 515. In step 520, a signal D is set to LPN (largest possible number) and the loop including steps 525, 530, 535 and 540 is entered to find the smallest distance of the distances dip'.

In decision step 525, the signal dip' representing the distance from sampled outlet Si and unsampled outlet Up is compared to D. When dip' is less than D, D is set to dip', Rm representing a tentative selected outlet is set to Si, the index i* is set to i and a tentative selected distance signal dmp is set to dip' in step 530. Step 535 is then entered in which sampled outlet index i is incremented. Where dip' is not less than D, step 535 is entered directly from decision step 525. Decision step 540 is then entered. Until sampled outlet index i exceeds imax in step 540, step 525 is reentered to compare the next distance signal dip' to the last determined minimum distance signal. When i exceeds imax, the minimum of the selected sampled outlets is chosen as Rm. The minimum distance signal dip' is then set to LPN in step 545 to exclude Si* from comparison in step 525 and the selected outlet index m is incremented in step 550.

Step 515 is reentered from step 555 until mmax closest outlets for unsampled outlet p are selected and another outlet Rm is chosen in the loop from step 525 through 540. Upon selection of mmax sampled outlets, the unsampled outlet index p is incremented in step 560 and step 510 is reentered via decision step 565 so that a set of m sampled outlets may be selected for the next unsampled outlet Up in FIG. 6 via decision step 565. When p is greater than pmax, control is passed to step 340 in FIG. 4.

In step 340, index p is set to one. A weighting factor $w_m$ is then determined for each selected sampled outlet Rm of unsampled outlet Up in step 345. Weighting factor generation is performed in the processor 215. The weighting factor is an inverse function of the distance between the sampled outlet Rm and the unsampled outlet Up and the characteristics of the sampled and unsampled outlets according to $$w_m = \{(1/d_{RmUp}{}^q)/(\Sigma(T_m/d_{RmUp}{}^q))\} * T_{Up} \quad (1)$$

where $d_{RmUp}$ is the distance between sampled outlet $S_m$ and unsampled outlet Up, the summation is over all sampled outlets for m=1 to mmax, $T_{up}$ is the unsampled outlet characteristic (e.g., total sales volume for all products), $T_m$ is the sampled outlet characteristic and q is greater than zero. q may, for example, be 2. Index p is incremented in step 348 and control is passed to step 345 until p is greater than pmax in decision step 350.

The weighting factor signals for unsampled outlets Up and the product data for the outlets are read into the transfer store 228 as a data array which is divided therein into N data array portions. The processor 215 sends control signals to work station processors 230-1 through 230-N to initiate processing of the data file portions in the work station processor. Each work station processor then proceeds to form a product estimate signal for the data file portion assigned to it as indicated with respect to the entire data file in steps 355 through 370 in FIG. 4. In step 355-1, a starting value of the unsampled outlet index p=1 is set. The loop from step 360-1 to step 370-1 is then entered. The estimated sales of the particular product is then generated for a range of unsampled stores Up in step 360 according to $$Est(V_{Up}) = \Sigma w_m V_m \quad (2)$$

where $V_m$ is the sales volume of the particular product at sampled outlet m and the summation is over the sampled outlets from m=1 to m=mmax. The unsampled outlet index p is incremented in step 365-1 and control is passed back to step 360-1 via decision step 370-1 until p is greater than the maximum of the range processed in work station processor 230-1 and an estimate of sales volume for all unsampled outlets in the range has been formed. The processing of the other work station processors 230-2 through 230-N is the same as described with respect to the work station processor 230-1 except that the range is determined by the portion of the data file sent to the work station. The processing in the work station processor 230-N is shown in the steps 355-N through 370-N.

For purposes of illustration with respect to FIG. 2, the number of selected sampled outlets mmax is chosen as 3. It is to be understood, however, that other values may be chosen. For example, if there are 50 or more sampled outlets, mmax=10 is a suitable value. In FIG. 2, sampled outlets O1, O2 and O3 are selected as the three closest sampled outlets R1, R2 and R3 to unsampled outlet U1. To illustrate the invention, assume that the distance $d_{R1U1}$ from sampled outlet R1 to unsampled outlet U1 is 0.4 miles, the distance $d_{R2U1}$ between sampled outlet R2 and unsampled outlet U1 is 0.2 miles and the distance $d_{R3u1}$ between sampled outlet R3 and unsampled outlet U1 is 0.6 miles. Further assume that the total sales volume for all products at sampled outlets R1, R2, R3 and U1 are $3,000, $2,000, $5,000 and $4,000, respectively. The weighting factor for sampled outlet R2 is then $$w_2=\{(1/0.2)^2/(2000/(0.2)^2+3000/(0.4)^2+5000/(0.6)^2)\}*4000 \quad (3)$$

$$w_2=1.210084$$

Similarly, $w_1=0.302521$ and $w_3=0.13445377$. For a sales volume of the particular product at R1, R2 and R3 of 5, 20 and 4, respectively, the estimated sales volume of the particular product at unsampled outlet U1 is $$Est(V_{U1})=w_1*v_{R1}+w_2V_{R2}+w_3v_{R3} \quad (4)$$

$$Est(V_{u1})=26.252$$

The product volume signals for the sampled outlets Si is then formed in step 372-1 through 372-N and the total estimated sales volume of the product for unsampled and the sampled outlets is then formed for each range in the work station processors 230-1 through 230-N in steps 375. The resulting unsampled outlet estimate and total volume estimate signals of the processing in the work station processors is then merged in and totaled step 380 into a result data file. The result data file is transferred to transfer store 228 and therefrom to data store 210. The results are then sent to output line 245 of the input/output 201.

Figure 7:
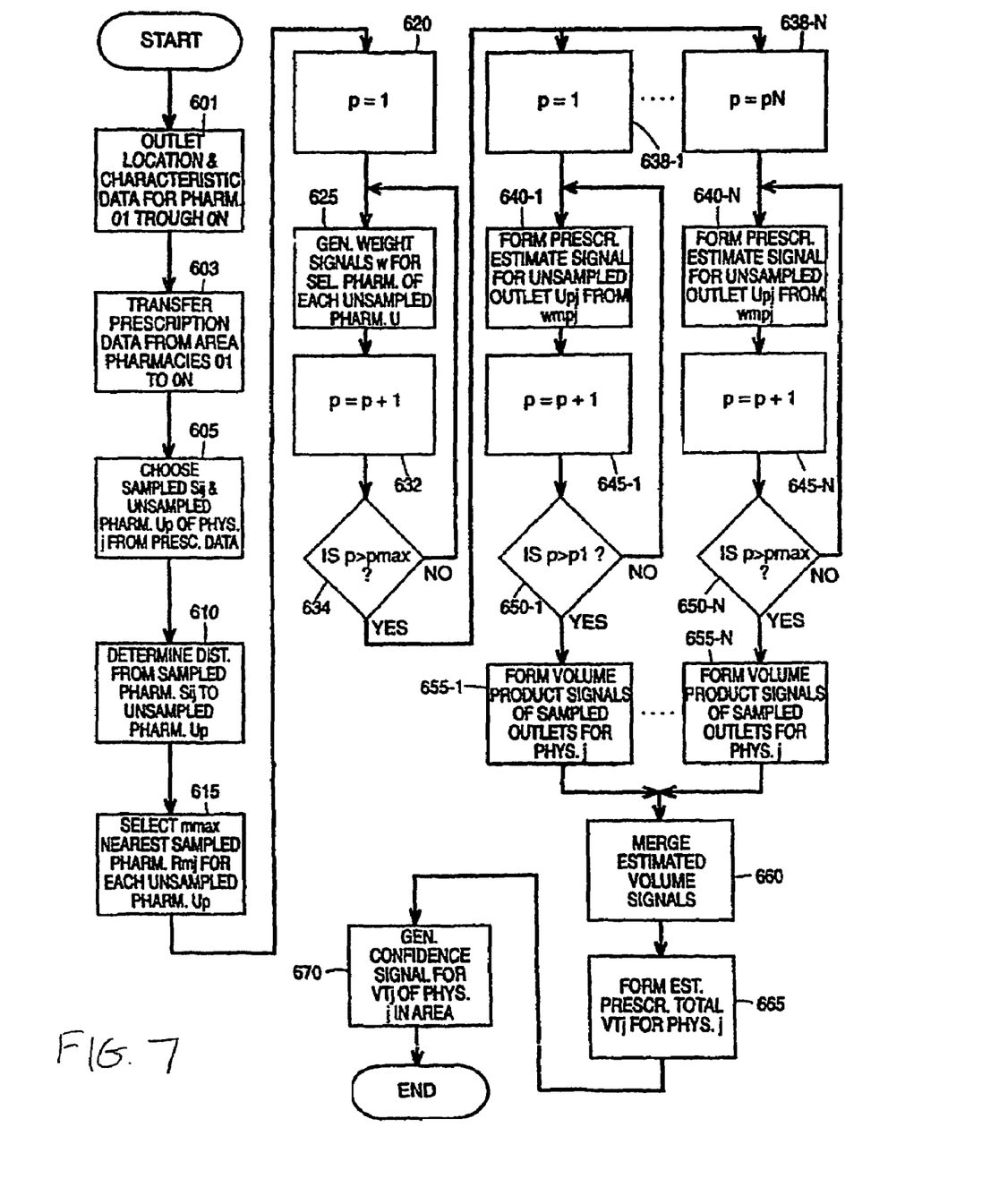
FIG. 7 is a flow chart showing one arrangement for the estimation of prescriptions sales for a prescribing physician at a plurality of pharmacies illustrative of the invention.

FIG. 7 shows a flow chart illustrating estimation of the distribution of a controlled product by a control authority. More particularly, FIG. 7 shows the operation of the arrangement of FIGS. 2 and 3 in estimating sales of a prescription product for a prescribing physician at the pharmacies. The operations in the flow chart of FIG. 7 are performed by processor 215 and work station processors 230-1 through 230-N of FIG. 3 under control of corresponding instruction signals stored in the program store 220. Referring to FIG. 7, location data, data of type characteristics of pharmacy outlets O1 through ON in FIG. 2 and physician identification data are stored in the characteristics and locations store 205 of FIG. 3 in step 601. Prescription data is transferred from pharmacies O1, O2, O3, ON-1 and ON and is stored in pharmacy outlet data store 210 according to the prescribing physicians (step 603).

At prescribed intervals, the total sales for the prescribing physician j of a particular prescription product is estimated in steps 605 through 670 of FIG. 7. In step 605, the processor 215 operates to determine the sampled pharmacy outlets Sij and the unsampled pharmacy outlets Up for a particular prescription product according to the validity and volume of the transferred prescription data of the prescribing physician j. The arrangement shown in FIG. 5 may be used in the determination of step 605. As described with respect to FIGS. 2 and 3, pharmacy outlets O1, O2, O3, ON-1 and ON can be determined as sampled outlets S1j, S2j, S3j, S4j and S5j where the sampled data is validated. Outlets O4 and O5 are classified as unsampled outlets U1 and U2.

Step 610 is entered from step 605 and signals representative of the distances dip between each sampled outlet Sij and each unsampled outlet Up are generated in the processor 215. After the distance determination of step 610, the set of nearest sampled pharmacy outlets Rmj for each unsampled pharmacy outlet Up is selected by processor 215 according to step 615. Selection of sampled pharmacies may be performed as described with respect to FIG. 6. Then, the unsampled pharmacy outlet index p is set to 1 in step 620 and a weighting factor signal wm for the each sampled pharmacy outlet Rm (m=1 to mmax) is generated in loop from step 625 to step 634. Each weighting factor signal is formed according to $$w_m=\{(1/d_{RmUp}^q)/(\Sigma(T_{Rm}/d_{RmUp}^q))\}*T_{Up} \quad (5)$$

where q is greater than 0, $T_{Up}$ is the total sales volume of all products at pharmacy outlet Up, $T_{Rm}$ is the total sales volume of all products at pharmacy outlet Rm and the summation Σ is from m=1 to mmax.

After the weighting factor signals have been formed for the last unsampled pharmacy in the loop from step 625 to 634, a data array including the weighting information and the sales data from store 210 is formed by the processor 215 and sent to transfer store 228. The data array is divided into N portions each of which is processed by one of work station processors 230-1 through 230-N to form a signal representing an estimate of the total prescription product sales volume for physician j. The operations of the work station processors are controlled by the processor 215 through the control line 245. Each work station processor operates to process a predetermined range of the data array in the transfer store 228.

The work station processor 230-1 operates according to steps 638-1 through 655-1 to form the volume product signals for physician j in the range p=1 to p=p1. In step 640-1, the prescription estimate signal for unsampled outlets Upj is formed for each unsampled pharmacy in the range from p=1 to p=p1 and the sales volume signal for the sampled pharmacies in this range is determined by the work station processor 230-1 according to step 655-1. Work station processor 230-N operates in similar manner for physician j over the range p=pN to p=pmax as indicated in FIG. 7 according to steps 638-N through 655-N. Signals are transferred from one work station processor to another as required for the operation of the one work station processor through the network 255. The results of the operation of work station processors 230-1 through 230-N are merged in step 660 and an estimate of the prescription product volume $$V_T=\Sigma_1 V_{Sij}+\Sigma_2 V_{jUp} \quad (6)$$

is generated in step 665 where $$V_{jUp}=\Sigma_3\{\{(1/d_{RmUp}^q)/(\Sigma_3(T_{Rm}/d_{RmUp}^q))\}*T_{Up}\{V_{Rmj} \quad (7)$$

$\Sigma_1$ is the summation over all sampled outlets, $\Sigma_2$ is the summation over all unsampled outlets, $\Sigma_3$ is the summation over all sampled outlets in the neighborhood of unsampled outlet Up. At this time, a confidence signal that estimates the degree of possible error of the total volume $V_{Tj}$ of the product prescriptions of the prescribing physician j is then generated in step 670.

Figure 8:
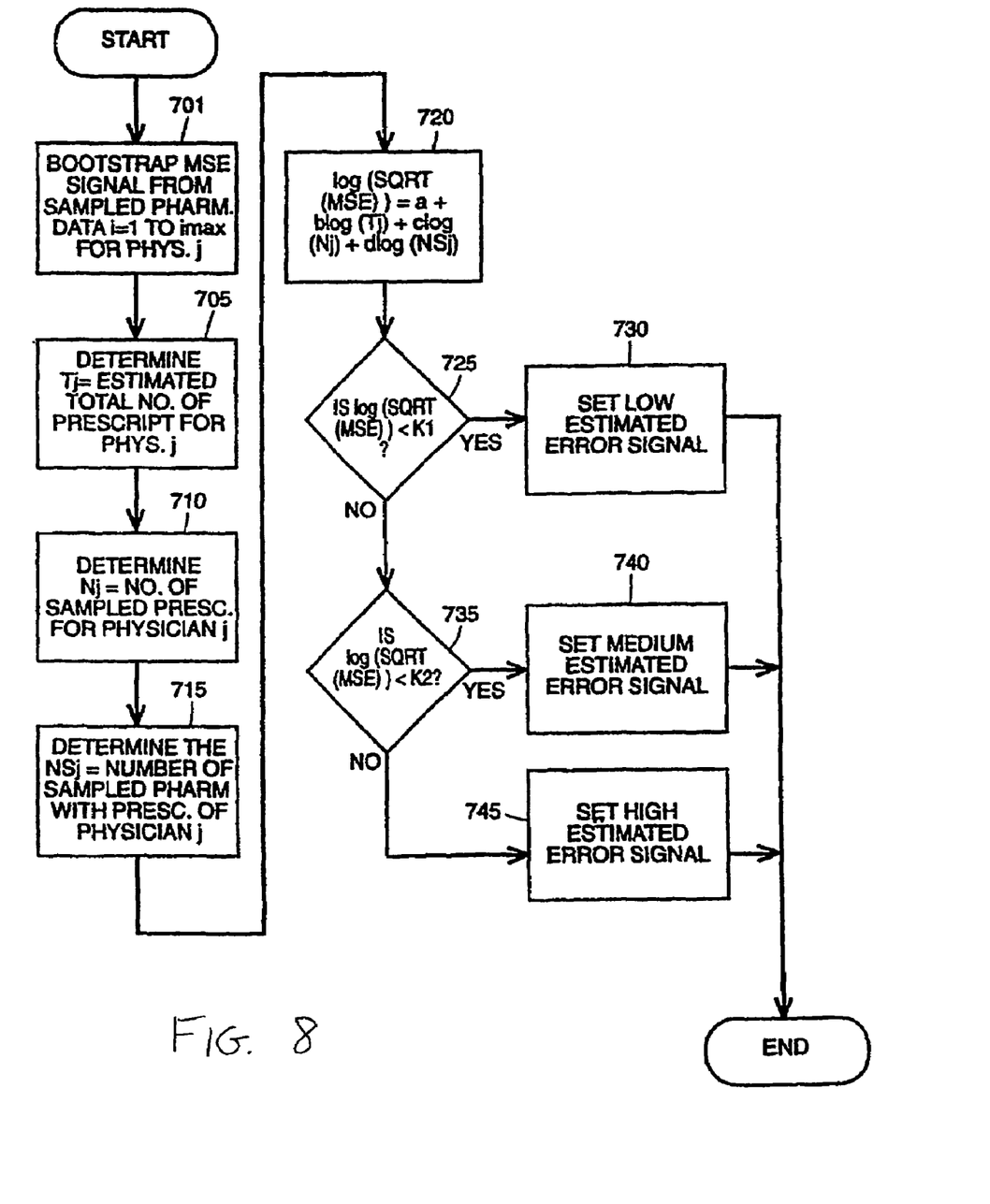
FIG. 8 is a flow chart showing the confidence signal operation of FIG. 7 in greater detail.

FIG. 8 shows the confidence signal generation operation of step 670 in greater detail. Referring to FIG. 8, a mean squared error signal MSE is first generated by bootstrapping on the basis of the sales data from the sampled pharmacy outlets S1 through Simax in step 701. The bootstrapping method is well known in the art and is described in "The Jacknife, The Bootstrap, and Other Resampling Plans" by B. Efron, Society for Industrial and Applied Mathematics (SIAM) Publications, Philadelphia 1982.

In the bootstrapping, subsets of pharmacy outlets are selected and the prescribing physician's prescription volume is estimated therefrom. The variances of the "bootstrapped" estimates closely approximates the true variance. A generalized variance function (GVF) is derived from the MSEs generated in step 701 of the form $$\log(SQRT(MSE))=a+b\log(T_j)+c\log(N_j)+d\log(N_{Sj}) \quad (8)$$

where SQRT is the square root, a, b, c and d are regression coefficients, $T_j$ is the estimated total of the prescription product prescribed by physician j, $N_j$ is the total of prescription products prescribed by physician j and dispensed at the sampled pharmacy outlets and $N_{Sj}$ is the number of sampled pharmacy outlets with prescription product sales for physician j. The generalized variance function is described in "Introduction to Variance Estimation" by K. M. Wolter, Springer-Verlag, New York 1985.

The values of $T_j$, $N_j$ and $NS_j$ are determined in steps 710, 715 and 720 from the prescription data in store 210 of FIG. 3 in processor 215. Regression coefficient signals a, b, c and d are generated by multiple regression techniques well known in the art and a log(SQRT(MSE)) value for the physician j is determined in step 720. Decision step 725 is then entered in which the value log(SQRT(MSE)) is compared to K1. If log(SQRT(MSE)) is less than K1, a low estimated error signal is produced in step 730. The value log(SQRT(MSE)) is then compared to K2>K1 in step 735 to produce a medium estimated error signal in step 740 if log(SQRT(MSE)) is less than K2. Where log(SQRT(MSE)) is not less than K2, a high estimated error signal is generated in step 745. While three values for the estimated error signal are determined in the flow chart of FIG. 8, it is to be understood that any number of values such of 5 may be used.

Figure 9:
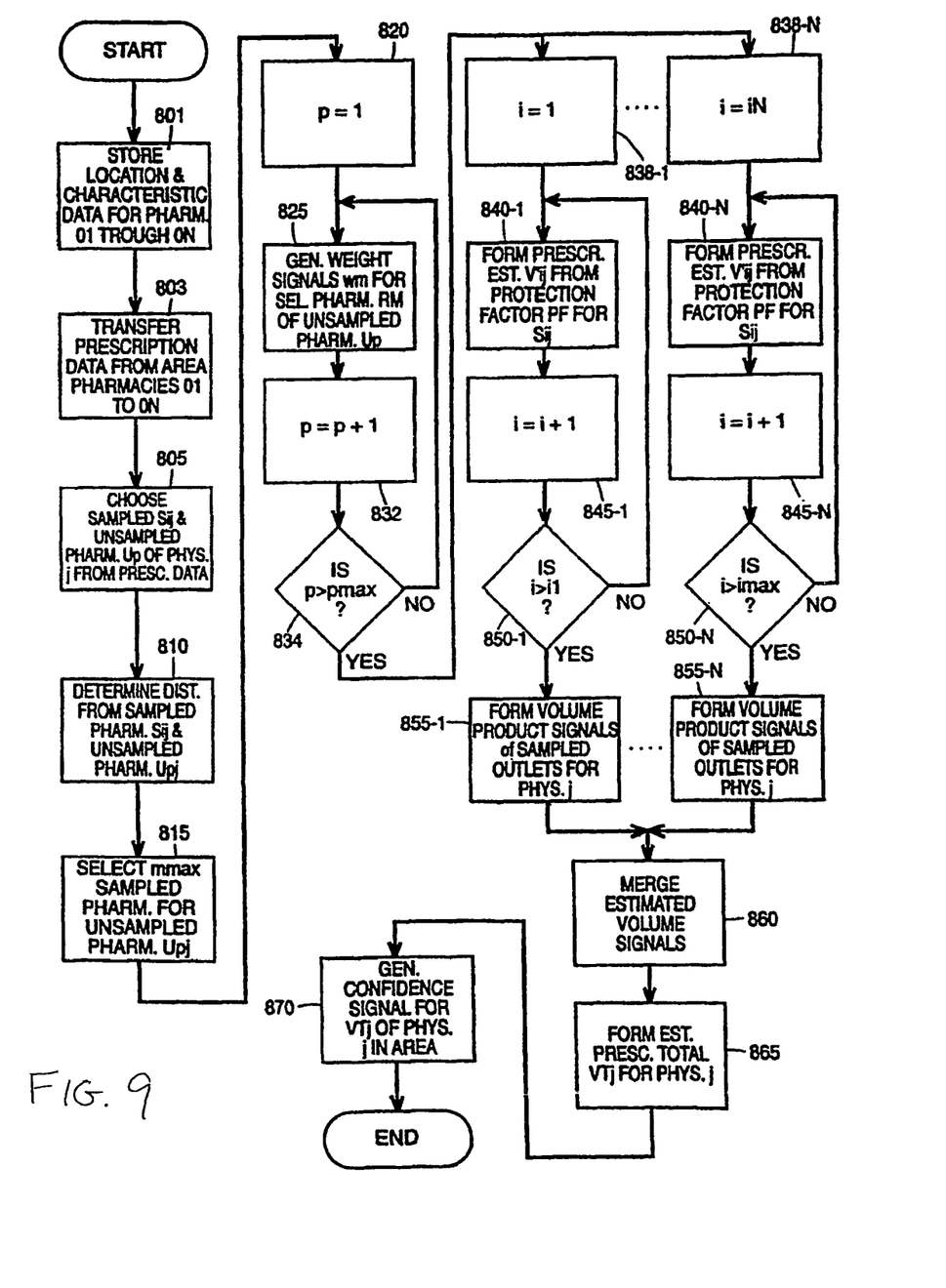
FIG. 9 is a flow chart showing another arrangement for the estimation of prescription sales for a prescribing physician at a plurality of pharmacies illustrative of the invention.

The flow chart of FIG. 9 illustrates another arrangement for estimating the prescription product sales volume of a prescribing physician. According to the arrangement of FIG. 9, a group of sampled pharmacies is selected for each unsampled pharmacy and a weighting factor for each sampled pharmacy in the neighborhood of one of the unsampled pharmacies is generated as in FIG. 7. The weighting factors for the sampled pharmacies are combined with the actual sales data for the sampled pharmacies according to $$V_{Tj}=\Sigma_1 V_{Sij}+\Sigma_2\Sigma_3 w_{sp}V_{Sij} \quad (9)$$

which corresponds to $$V_{Tj}=\Sigma\Sigma_1 V_{Sij}[1+\Sigma_4 w_{ip}] \quad (10)$$

where $V_{Sij}$ is the prescription product sales volume for physician j at pharmacy i, $w_{ip}$ is the weighting factor for a sampled pharmacy i in the selected neighborhood of unsampled pharmacy p, $\Sigma_1$ is the summation over all sampled pharmacies and $\Sigma_2$ is the summation over all unsampled pharmacies, $\Sigma_3$ is the summation of all sampled pharmacies in the neighborhood of unsampled pharmacy p and $\Sigma_4$ is the summation of weighting factors associated with sampled pharmacy i. The resulting estimate of sales volume for the prescribing physician is similar to that described with respect to FIG. 7 but the efficiency of the estimate generation is improved.

In the method of FIG. 9, the sampled pharmacies in the neighborhood of each sampled pharmacy are first determined and the weighting factor signals $w_{ip}$ for the neighborhood sampled pharmacies are formed in the processor 215 of FIG. 3 on the basis of the pharmacy location, the characteristics data and the physician identification data in store 205. The sales data from the sampled pharmacies and the weighting factor signals $w_{ip}$ are transferred to the transfer store 228, divided therein into prescribed ranges and each range of data is supplied to an assigned one of the work station processor 230-1 through 230-N. In each work station processor, the estimated sales volume for each sampled pharmacy outlet in range processed by the work station processor is generated from the sales data and the projection factor for the sampled pharmacy outlet. The total estimated sales volume for the sampled pharmacy outlets over range of the work station processor is then generated. When the work station processing is completed the resulting estimated sales volumes from the work station processors are merged and transferred via the transfer store 228 to the processor 215.

Referring to FIG. 9, the locations, type characteristics of pharmacy outlets O1 through ON in FIG. 2 and physician identification data are stored in the characteristics and locations store 205 of FIG. 3 in step 801. Prescription data is received from the pharmacies O1, O2, O3, ON-1 and ON and is stored in data store 210 according to the prescribing physicians (step 803).

The total sales for the prescribing physician j of a particular prescription product is estimated in steps 805 through 870. In step 805, the processor 215 operates to identify the sampled pharmacy outlets Sij and the unsampled pharmacy outlets Up for a particular prescription product according to the validity and volume of the transferred prescription data of the prescribing physician j. The arrangement shown in FIG. 5 may be used. As described with respect to FIGS. 2 and 4, pharmacy outlets O1, O2, O3, ON-1 and ON can be determined as sampled outlets S1j, S2j, S3j, S4j and S5j where the sampled data is validated. Outlets O4 and O5 are classified as unsampled outlets U1 and U2.

Step 810 is entered from step 805 and signals representative of the distances dip between each sampled outlet Sij and each unsampled outlet Up are generated in the processor 215. After the distance determination of step 810, the set of nearest sampled pharmacy outlets Rmj for each unsampled pharmacy outlet Up is selected by processor 215 according to step 815. The selection of sampled pharmacies Rmj may be performed as previously described with respect to FIG. 6.

The unsampled pharmacy index p is reset to one in step 820 and weighting signals wmp are formed for the selected sampled pharmacies Rmi in the loop from step 825 to 834. In step 825, the weighting signal $$w_{mp}=\{(1/d_{RmUp}^q)/(\Sigma(T_m/d_{RmUp}^q)\}*T_{Up} \quad (11)$$

is formed for each sampled pharmacy m selected as in the neighborhood of sampled pharmacy Up. After the weighting signals for all unsampled pharmacies are formed in the processor 215, the sales data stored in store 210 and the weighting signals are transferred to transfer store 228 wherein the data and weighting signal array is divided into N portions and each portion is transferred to one of work station processors 230-1 through 230-N. The processing of the portion transferred to work station processor 230-1 is shown from step 838-1 through 855-1 in FIG. 9 and the processing the portion transferred to work station processor 230-N is indicated from step 838-1 to 838-N.

With respect to the processing of the range of sampled pharmacies in work station processor 230-1, the sampled pharmacy index i is set to one in step 838-1 and the loop from step 840-1 through 850-1 is iterated to form the estimated prescription volume $V'_{ij}$ for the sampled pharmacies in the range from i=1 to i=i1. In each iteration, an estimated volume signal is generated for sampled pharmacy i in step 840 according to $$VT_{Sij}=V_{Sij}[1+\Sigma w_{mp}] \quad (12)$$

where $V_{Sij}$ is the actual prescription product sales volume for physician j at pharmacy i, $w_{mp}$ are the weighting factor for sampled pharmacy Sij and $\Sigma$ is the summation over all weighting factors associated with the pharmacy Sij. $[1+\Sigma w_{mp}]$ is a projection factor for a physician's prescription at the sampled pharmacy $V_{Sij}$.

After the estimated volume signal is formed for the range i=1 to i1 in the work station processor 230-1, step 855-1 is entered from step 850-1 wherein the total volume for the range from i=1 to i=i1 by summing the estimated volumes for the pharmacies Sij. The work station processor 230-N operates in similar manner from step 838-N to 855-N to generate a total estimated volume for the range from iN to imax. Work station processors are interconnected by the network 250 such as an ethernet or token ring arrangement so that signals from one work station processor that are required for the formation of the $VT_{TSij}$ signal in another work station are transferred. The total volume signals for the ranges are merged in step 860 and the merged signals are transferred to the processor 215 via the transfer store 228. The resulting estimated total volume signal $V_{Tj}$ for the physician j is then formed in the processor 215 (step 865) and a confidence signal for the estimated total volume $V_{Tj}$ is generated in step 870 as described with respect to the flow chart of FIG. 8.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

What is claimed is:

1. A data analysis system for evaluating the performance of a first at-least one of a plurality of pharmacy outlet(s) in a pharmacy chain, there being several such pharmacy chains in the marketplace, the system comprising:
    a computer system coupled to a centralized database common to all the pharmacy chains in the marketplace, wherein the database houses:
    (1) confidential pharmaceutical information related to all the pharmacy chains, wherein the confidential information related to a particular pharmacy chain includes market measures of its plurality of pharmacy outlets, and
    (2) reference files including industry-standard market measures;
    (3) a plurality of data records, wherein each of the data records includes an outlet name, an organization name, and a parent name; and
    a data access application providing user/outlet-access to the database from a second one of the plurality of pharmacy outlets, wherein the data access application is configured to provide user/outlet access to (a) reference files including the industry-standard market measures, and (b) only to data associated with the second one of the plurality of pharmacy outlets' pharmacy chain while keeping the confidential information related to other pharmacy chains inaccessible.

2. The data analysis system of claim 1, wherein at least one of the plurality of outlets is a retail sales location.

3. The data analysis system of claim 1, wherein at least one of the plurality of outlets is a pharmaceutical sales location.

4. The data analysis system of claim 1, wherein the computer system receives market measures from the portion of the plurality of outlets through the transceiver.

5. The data analysis system of claim 4, wherein the computer system receives the market measures from users utilizing the data access application.

6. The data analysis system of claim 4, wherein the computer system generates industry-standard market measures based at least in part on the market measures from the portion of the plurality of outlets.

7. The data analysis system of claim 1 wherein the pharmacy chain is associated with at least one of the plurality of outlets associated with a particular organization name.

8. A method for evaluating the performance of at least one of a plurality of pharmacy outlets in a pharmacy chain, there being several such pharmacy chains in the marketplace comprising the steps of:
    (a) receiving a username and password from a user associated with a second pharmacy outlet;
    (b) verifying that the username and password correspond to a user account, wherein the user account includes a reference to the pharmacy chain to which the second pharmacy outlet belongs;
    (c) receiving a request for a report comparing data associated with at least one outlet associated with the pharmacy chain to industry-standard market measures;
    (d) if the first and second pharmacy outlets belong to a common pharmacy chain, accessing a database that houses: confidential pharmaceutical information related to all the pharmacy chains, wherein the confidential information related to a particular pharmacy chain includes market measures of its plurality of pharmacy outlets, and reference files including industry-standard market measures;
    wherein accessing the database comprises accessing only the confidential information related to the common pharmacy chain and the reference files including industry-standard market measures to generate the report;
    (e) receiving data describing at least one of the plurality of outlets, wherein the data describing each of the at least one of the plurality of outlets includes an outlet name, an organization name, and a parent name
    (f) transmitting the report to the user.

9. The method of claim 8, further comprising the step of: (e) receiving market measures corresponding to one of the at least one outlet associated with the pharmacy chain.

10. The method of claim 9, wherein the market measures include all pertinent transactions from the one of the at least one outlet.

11. The method of claim 8, wherein at least one of the plurality of outlets is a retail sales location.

12. The method of claim 8, wherein at least one of the plurality of outlets is a pharmaceutical sales location.

13. The method of claim 8, further comprising the step of: (f) receiving market measures from the portion of the plurality of outlets.

14. The method of claim 13, further comprising the step of: (g) generating industry-standard market measures based at least in part on the market measures received from the portion of the plurality of outlets.

15. The method of claim 11, further comprising the step of: (i) storing a plurality of data records following the step (h), wherein each of the plurality of data records includes an outlet name, an organization name, and a parent name.

16. The method of claim 11, wherein the pharmacy chain is associated with at least one of the plurality of outlets associated with a particular parent name.

17. The method of claim 11, wherein the pharmacy chain is associated with at least one of the plurality of outlets associated with a particular organization name.

* * * * *